United States Patent
Lee et al.

(10) Patent No.: US 11,460,458 B2
(45) Date of Patent: Oct. 4, 2022

(54) ARTICLE STORAGE APPARATUS AND METHOD OF IDENTIFYING CONDITION OF ARTICLE THEREIN

(71) Applicant: Samsung Electronics Co., Ltd., Suwon-si (KR)

(72) Inventors: Kyounghoon Lee, Suwon-si (KR); Jongsoo Hong, Suwon-si (KR); Junhoe Choi, Suwon-si (KR); Jeongsu Han, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 319 days.

(21) Appl. No.: 16/851,892

(22) Filed: Apr. 17, 2020

(65) Prior Publication Data

US 2020/0333310 A1 Oct. 22, 2020

(30) Foreign Application Priority Data

Apr. 19, 2019 (KR) .................. 10-2019-0045817

(51) Int. Cl.
*G01N 33/02* (2006.01)
*G01N 33/00* (2006.01)

(52) U.S. Cl.
CPC ......... *G01N 33/02* (2013.01); *G01N 33/0016* (2013.01); *G01N 33/0044* (2013.01); *G01N 33/0047* (2013.01); *G01N 33/0054* (2013.01); *G01N 33/0062* (2013.01)

(58) Field of Classification Search
CPC .............. G01N 33/02; G01N 33/0016; G01N 33/0044; G01N 33/0054; G01N 33/0062
See application file for complete search history.

(56) References Cited

U.S. PATENT DOCUMENTS

| 2004/0166679 A1* | 8/2004 | Kishkovich ....... H01L 21/67253 438/689 |
| 2017/0263100 A1 | 9/2017 | Johnston |
| 2018/0196401 A1 | 7/2018 | Lagares-Greenblatt et al. |

FOREIGN PATENT DOCUMENTS

| CN | 108872493 A | * 11/2018 | ........... F25D 29/008 |
| CN | 110940779 A | * 3/2020 | |
| JP | 6-34613 A | 2/1994 | |
| JP | 3103985 B2 | * 10/2000 | |
| JP | 2003-172565 A | 6/2003 | |
| JP | 2003172565 A | * 6/2003 | |
| JP | 2018-96712 | 6/2018 | |

(Continued)

OTHER PUBLICATIONS

International Search Report dated Aug. 7, 2020, in corresponding International Patent Application No. PCT/KR2020/005215.

*Primary Examiner* — Nathaniel J Kolb
(74) *Attorney, Agent, or Firm* — Staas & Halsey LLP

(57) ABSTRACT

An article storage apparatus includes a sensor device sensing gases included in air in a chamber where an article is stored; a concentrator concentrating the gases contained in the air; a filtering device filtering the gases contained in the air; and at least one processor. The at least one processor controls the concentrator to concentrate the gases contained in the air, and identifies a condition of the article based on a concentration level of a target gas related to the article measured by the sensor device when the target gas is extracted as gases desorbed from the concentrator pass the filtering device.

17 Claims, 12 Drawing Sheets

(56) References Cited

FOREIGN PATENT DOCUMENTS

| JP | 2021165604 A | * | 10/2021 |
|----|--------------|---|---------|
| KR | 10-2014-0086703 A | | 7/2014 |
| KR | 10-1744462 | | 6/2017 |
| KR | 101809224 B1 | * | 1/2018 |
| KR | 10-2018-0047713 | | 5/2018 |

* cited by examiner

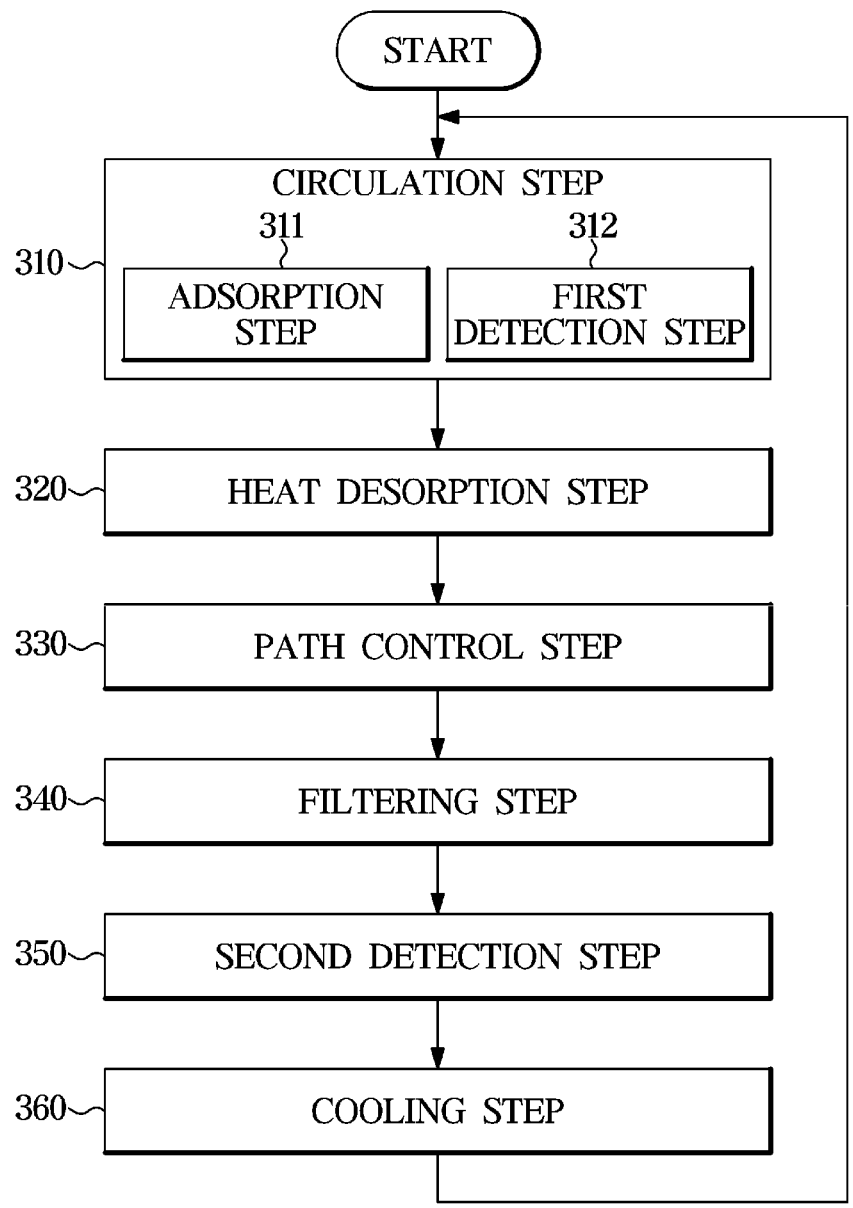

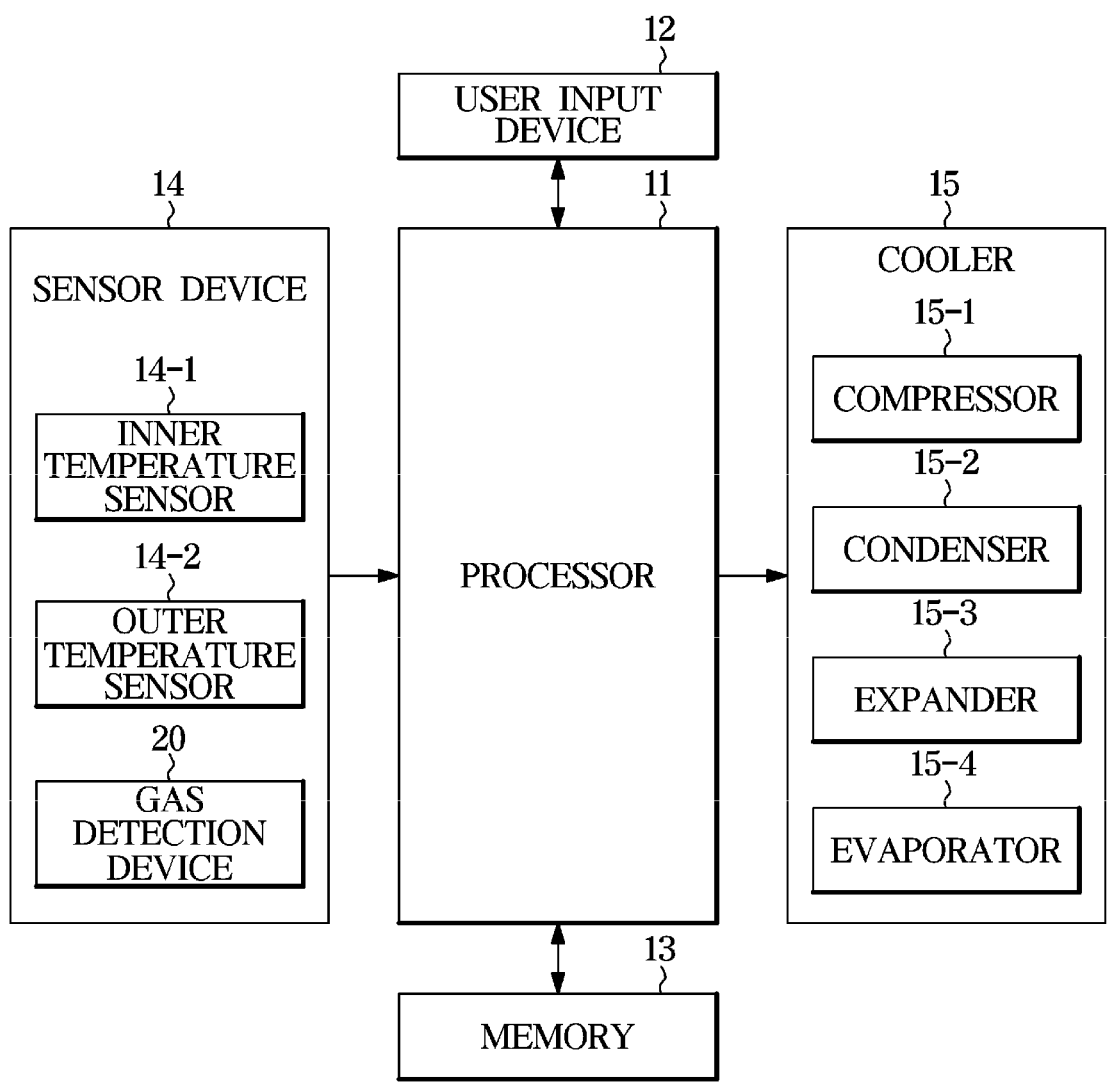

ARTICLE STORAGE APPARATUS AND METHOD OF IDENTIFYING CONDITION OF ARTICLE THEREIN

CROSS-REFERENCE TO RELATED APPLICATION

This application is based on and claims priority under 35 U.S.C. § 119 to Korean Patent Application No. 10-2019-0045817 filed on Apr. 19, 2019, the disclosure of which is incorporated herein by reference in its entirety.

BACKGROUND

1. Field of the Invention

The disclosure relates to an article storage apparatus and method of identifying a condition of an article stored in the article storage apparatus.

2. Discussion of Related Art

An article storage apparatus is a device for storing articles, such as a refrigerator or a garment care device.

For example, the refrigerator is a device for keeping foods fresh by supplying cold air into its storeroom. Spoiling of the food stored in the refrigerator may be delayed to a certain extent, but the food may ripen or may be spoiled in the end as time goes on. When the food is spoiled, many different types of gases may be produced. For example, gases such as ammonia, hydrogen sulfide, methane, etc., may be produced from decomposition of a food by micro organism.

People may determine a degree of decaying of a food kept in the refrigerator by smell or with naked eyes. In this case, they often make wrong decision and eat spoiled food, ending up suffering from an infectious or toxic disease such as food poisoning. Hence, a plan to predict a condition of a food and ensure people to have the food safely is being studied. For example, a study on a method of predicting a condition of a food by detecting a gas produced from the food is being conducted.

The existing method of identifying a condition of an article (e.g., a food) using a gas sensor detects only a high concentration chemical gas (e.g., in hundreds of ppb or more) but hardly detects a low concentration chemical gas (e.g., in tens of ppb).

Furthermore, the gas produced from an article (e.g., a food) may often be a mixture of various types of gases, and the method has difficulty in selecting a particular gas from the various kinds of gases and predicting a condition of the food.

Moreover, the method requires an extra pre-process to be performed by the user to collect a gas or an extra large size device to collect the gas.

Hence, a more effective method for identifying a condition of an article stored in an article storage device may be required.

SUMMARY OF THE INVENTION

According to an aspect of the disclosure, an article storage apparatus includes a sensor device sensing gases included in air in a chamber where an article is stored; a concentrator concentrating the gases contained in the air; a filtering device filtering the gases contained in the air; and at least one processor. The at least one processor may control the concentrator to concentrate the gases contained in the air, and identify a condition of the article based on a concentration level of a target gas related to the article measured by the sensor device when the target gas is extracted as gases desorbed from the concentrator pass the filtering device.

According to another aspect of the disclosure, a method of identifying a condition of an article in an article storage apparatus includes concentrating gases contained in air in a chamber where an article is stored on an absorbent; extracting a target gas by filtering gases desorbed from the absorbent; detecting the extracted target gas and measuring a concentration level of the target gas; and identifying a condition of the article based on the measured concentration level of the target gas.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which:

FIG. 3 is a flowchart illustrating operation of an article storage apparatus, according to an embodiment of the disclosure;

FIG. 11 is a block diagram of an article storage apparatus, according to another embodiment of the disclosure.

DETAILED DESCRIPTION OF EXEMPLARY EMBODIMENTS

Figure 1:
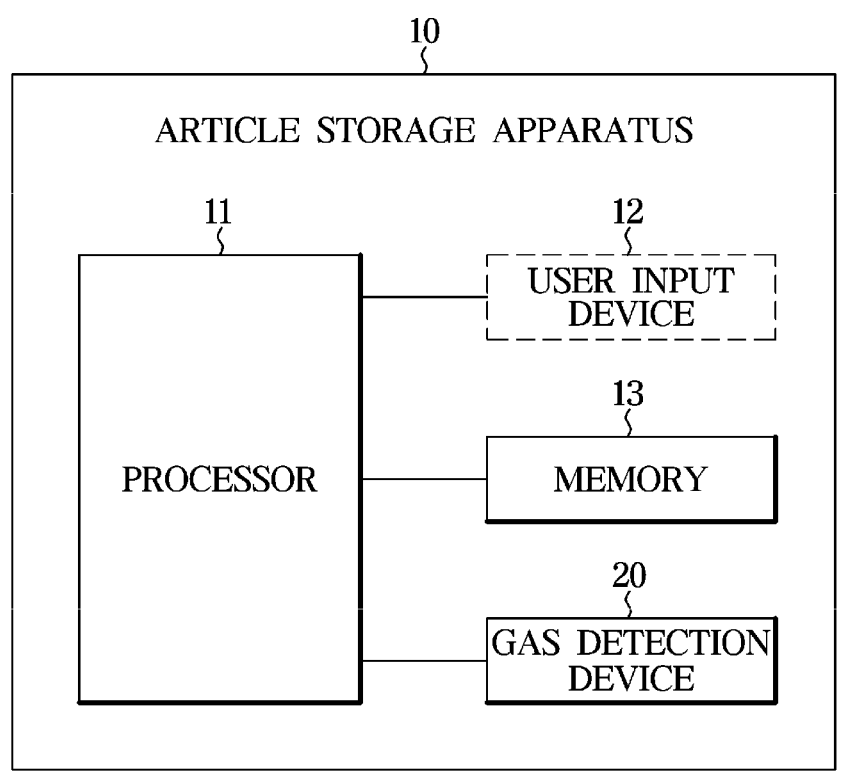
FIG. 1 is a block diagram of an article storage apparatus, according to an embodiment of the disclosure.

Like numerals refer to like elements throughout the specification. Not all elements of embodiments of the disclosure will be described, and description of what are commonly known in the art or what overlap each other in the embodiments of the disclosure will be omitted.

It will be further understood that the term "connect" or its derivatives refer both to direct and indirect connection, and the indirect connection includes a connection over a wireless communication network.

The term "include (or including)" or "comprise (or comprising)" is inclusive or open-ended and does not exclude additional, unrecited elements or method steps, unless otherwise mentioned.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section.

It is to be understood that the singular forms "a," "an," and "the" include plural references unless the context clearly dictates otherwise.

Reference numerals used for method steps are just used for convenience of explanation, but not to limit an order of the steps. Thus, unless the context clearly dictates otherwise, the written order may be practiced otherwise.

FIG. 1 is a block diagram of an article storage apparatus 10, according to an embodiment of the disclosure.

The article storage apparatus 10 may be, for example, a device for keeping foods such as a refrigerator or heating cabinet, or a device for managing/keeping garments such as a garment care device (e.g., Airdresser™), without being limited thereto. For example, the article storage apparatus 10 may be a device for keeping an animal or microorganism or incubating/breeding/isolating the stored one. In this case, air inside the article storage apparatus 10 may be referred to as air in the chamber.

When the article storage apparatus 10 is a refrigerator, the refrigerator may be classified by type based on the form of its storeroom and door. There may be a top mounted freezer (TMF) typed refrigerator in which a storeroom is partitioned by a horizontal partition wall into upper and lower chambers with a freezer formed in the upper chamber and a fridge formed in the lower chamber, and a bottom mounted freezer (BMF) typed refrigerator in which a fridge is formed in the upper chamber and a freezer is formed in the lower chamber. Furthermore, there may be a side by side (SBS) typed refrigerator in which a storeroom is partitioned by a vertical partition wall into left and right chambers with a freezer formed in one chamber and a fridge formed in the other chamber, and a French door refrigerator (FDR) typed refrigerator in which a storeroom is partitioned by a horizontal partition wall into upper and lower chambers with a fridge formed in the upper chamber and a freezer formed in the lower chamber.

The article storage apparatus 10 may include a processor 11, a memory 13, and a gas detection device 20, and optionally include a user input device 12.

The processor 11 may control general operation of the article storage apparatus 10. A specific example of the processor 11 will be described later with reference to FIG. 11.

Figure 2:
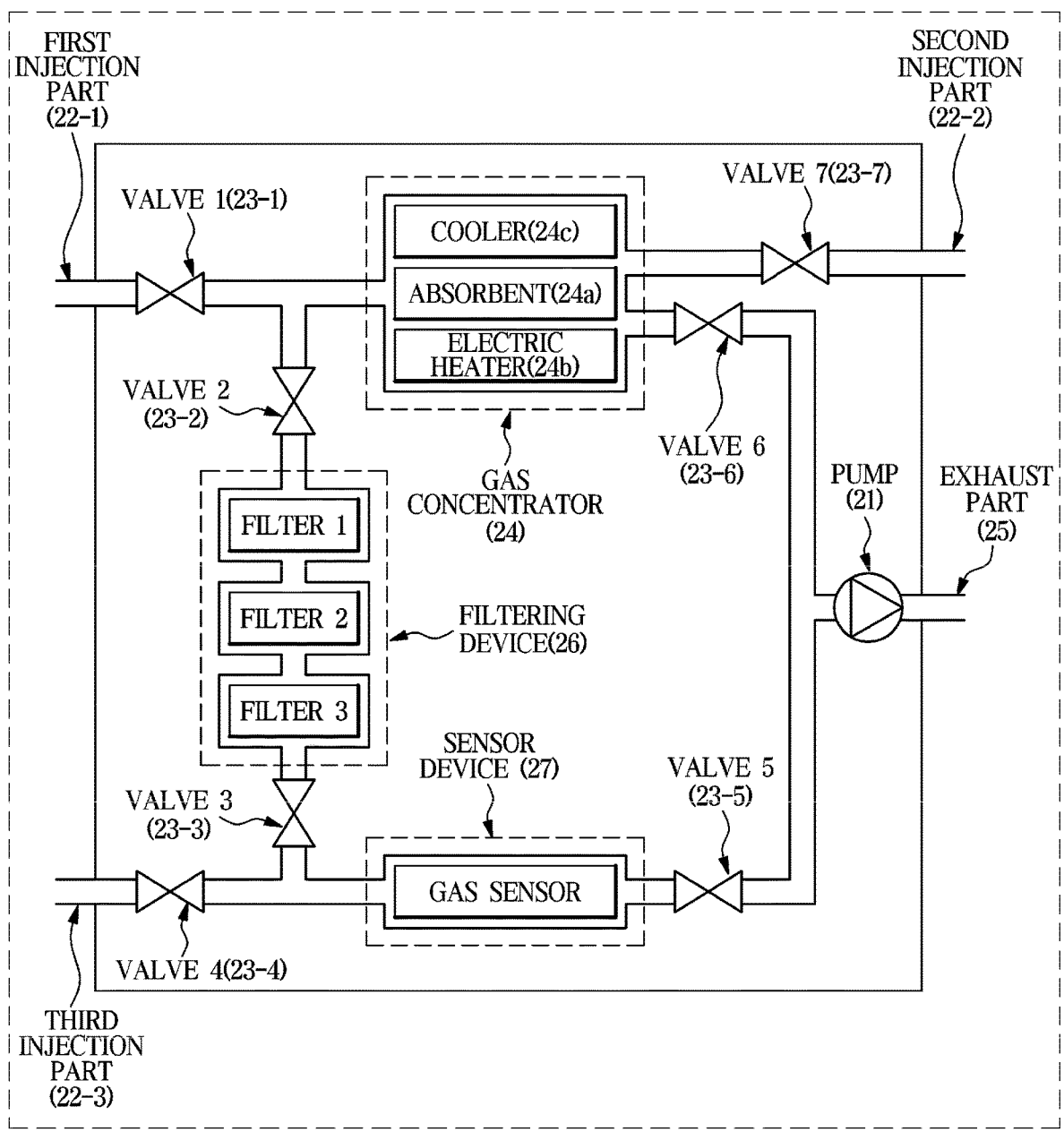
FIG. 2 is a block diagram of a gas detection device, according to an embodiment of the disclosure.

The processor 11 may replace at least some of the functions of a processor (not shown) of the gas detection device 20 of FIG. 2.

In an embodiment of the disclosure, the processor 11 may control a gas concentrator 24 (see FIG. 2) of the gas detection device 20 to concentrate gases included in the air, and identify a condition of an article based on concentration of a target gas measured by a sensor device 27 (see FIG. 2) when the target gas related to the article is extracted as the gases desorbed from the gas concentrator 24 pass a filtering device 26 (see FIG. 2).

The memory 13 may store a program and/or data required to execute the processor 11. A specific example of the processor 13 will be described later with reference to FIG. 11.

In an embodiment of the disclosure, the memory 13 may store at least one instruction for the processor 11 to control the gas concentrator 24 of the gas detection device 20 to concentrate gases included in the air, and identify a condition of an article based on concentration of a target gas measured by the sensor device 27 when the target gas related to the article is extracted as the gases desorbed from the gas concentrator 24 pass the filtering device 26. The at least one instruction may be loaded onto the memory 13 in the stage of manufacturing the article storage apparatus 10 or distributed online. For example, the at least one instruction may be downloaded from a server of the manufacturer or an application store onto the memory 13.

The user input device 12 may receive various input commands from the user. A specific example of the user input device 12 will be described later with reference to FIG. 11.

In an embodiment of the disclosure, the user input device 12 may enter e.g., a type of an article in the chamber, or receive a user input of selecting an article from among a plurality of article candidates.

The gas detection device 20 may detect whether there is a particular gas included in the air in the chamber or detect the concentration of the particular gas. Components of the gas detection device 20 will be described below in detail in connection with FIG. 2.

FIG. 2 is a block diagram of the gas detection device 20, according to an embodiment of the disclosure.

Referring to FIG. 2, the gas detection device 20 may include a pump 21, a plurality of injection parts 22-1, 22-2, and 22-3, a plurality of valves 23-1, 23-2, 23-3, 23-4, 23-5, 23-6, and 23-7, a gas concentrator 24, the filtering device 26, the sensor device 27, and an exhaust part 25, but at least one of the components may be omitted or a new component may be added in some other embodiments of the disclosure. At least one of the pump 21, the plurality of valves 23-1 to 23-7, the gas concentrator 24, the filtering device 26, or the sensor device 27 may be controlled by the processor 11 of the article storage apparatus 10 or a processor (not shown) of the gas detection device 20.

The pump 21 may suck the air in the chamber to the inside of the gas detection device 20. For example, the pump 21 may suck the air in a space where the gas detection device 20 is installed to the inside of the gas detection device 20.

The plurality of injection parts 221-1 to 22-3 may be passages through which the air sucked in by operation of the pump 21 is injected.

The plurality of valves 23-1 to 23-7 may guide flow paths for the air. For example, the plurality of valves 23-1 to 23-7 may repeat being opened and closed under the control of the processor 11 of the article storage apparatus 10 or the processor of the gas detection device 20 to guide flow paths for the air. In this case, at least some of the processor 11 of the article storage apparatus 10 or the processor of the gas detection device 20 may be referred to as a fluid path controller.

The gas concentrator 24 may concentrate a target gas from the circulating air. The target gas may be a gas related to freshness of a food, including for example, at least one of ammonia, trimethylamine or dimethyl sulfide, without being limited thereto.

The gas concentrator 24 may include an absorbent 24a for absorbing the target gas contained in the air. The absorbent 24*a* may include, for example, at least one of poly dimethyl siloxane, zeolite, or Tenax TA, which may be a composite material coated with at least one of carbon material, porphyrin, or phthalocyanine and having improved selective absorbability for the target gas. The absorbent 24*a* may be provided in a small container. The small container may be formed with stainless steel, glass, quartz, or silicon, without being limited thereto.

Furthermore, the gas concentrator 24 may further include an electric heater 24*b* for desorbing the gas adsorbed on the adsorbent 24*a*, and a cooler 24*c* for cooling down the temperature of the absorbent 24*a* heated by the electric heater 24*b*.

The filtering device 26 may filter out other gases than the target gas from the gases desorbed from the adsorbent 24*a* by the electric heater 24*b*. The filtering device 26 may include at least one or more filters, each having a different structure (e.g., in a column or sifter type) or using a different filtering component. The filtering component may include, for example, Tenax TA, a carbon material, zeolite, Anodized Aluminum Oxide (AAO), or a porous material such as a metal organic framework (MOF), and the filtering component may be coated with porphyrin, phthalocyanine or carbon-based nanomaterial.

The sensor device 27 may detect an injected gas and measure the concentration of the gas. The sensor device 27 may include, for example, at least one of a semiconductor gas sensor, an electrochemical gas sensor, a catalytic combustive gas sensor, a heat conductive gas sensor, or an optical gas sensor. The sensor device 27, the processor 11, or the processor of the gas detection device 20 may measure at least one of a type or a concentration level of a gas by analyzing patterns of a signal sensed by at least one sensor.

The exhaust part 25 may be a passage through which the air injected to the gas detection device 20 is discharged out of the gas detection device 20.

Again, the gas detection device 20 may further include the processor. The processor may control general operation of the gas detection device 20.

When there is the processor equipped in the gas detection device 20, the gas detection device 20 may further include a communication device (not shown). In this case, the processor of the gas detection device 20 may control at least one of the pump 21, the plurality of valves 23-1 to 23-7, the gas concentrator 24, the filtering device 26, or the sensor device 27, based on a control signal provided through the communication device from the processor 11 of the article storage apparatus 10.

The processor of the gas detection device 20 may also provide a signal obtained from the sensor device 27 through the communication device to the processor 11 of the article storage apparatus 10. The processor 11 of the article storage apparatus 10 may identify a condition of an article kept in the article storage apparatus 10 based on the signal obtained from the gas detection device 20.

The at least one processor as herein used may refer to the processor 11 of the article storage apparatus 10 or both the processor 11 of the article storage apparatus 10 and the processor of the gas detection device 20.

In an embodiment of the disclosure, the at least one processor may control the gas concentrator 24 to concentrate gases contained in the air in the chamber, and identify a condition of an article based on concentration of a target gas related to the article kept in the article storage apparatus 10 measured by the sensor device 27 when the target gas is extracted as the gases desorbed from the gas concentrator 24 pass through the filtering device 26.

Furthermore, the at least one processor may close or open at least one of the plurality of valves so as for the air in the chamber to pass the gas concentrator 24 along a first flow path, and close or open at least one of the plurality of valves so as for the gases desorbed from the gas concentrator 24 to pass the filtering device 26 and then the sensor device 27 along a third flow path, which is different from the first flow path.

Moreover, the at least one processor may identify at least one of a type or a condition of the article based on the concentration level of all the gases included in the air in the chamber measured by the sensor device 27 while the gases included in the air are being concentrated. In this case, a detection cycle of the sensor device 27 for measuring the concentration level of all the gases may be shorter than that for measuring the concentration level of the target gas.

Furthermore, the at least one processor may close or open at least one of the plurality of valves so as for the air in the chamber to pass the sensor device 27 along a second flow path.

The at least one processor may control the electric heater 24*b* to heat the absorbent 24*a* so as to desorb the gases adsorbed on the adsorbent 24*a* and control the cooler 24*c* to cool the heated absorbent 24*a*.

Furthermore, the at least one processor may identify a type of an article based on a user input through the user input device 12, and set threshold values required to identify a condition of the article based on the type of the article.

Moreover, the at least one processor may control a display (not shown) to display information about the article condition indicating the condition of the article.

FIG. 3 is a flowchart illustrating operation of the article storage apparatus 10, according to an embodiment of the disclosure.

Figure 4A:
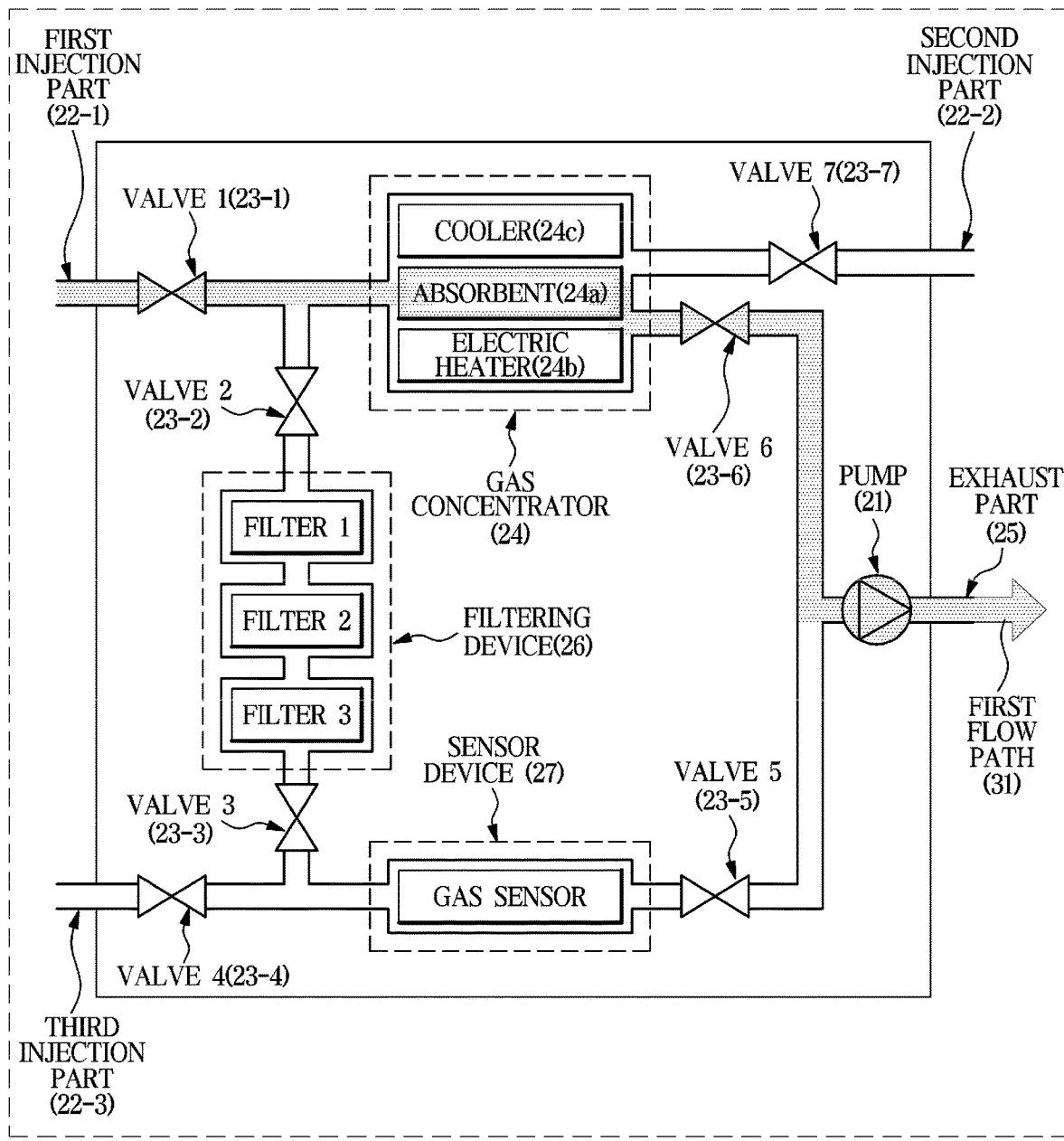
FIG. 4A shows a circulation process of air inside a gas detection device, according to an embodiment of the disclosure.

Referring to FIG. 3, the article storage apparatus 10 may perform a circulation step 310 in which the air in the chamber is injected to the gas detection device 20, circulated in the gas detection device 20, and discharged to the outside. The circulation step 310 may include an adsorption step 311 in which the air in the chamber flows along the first flow path 31 as shown in FIG. 4A, and a first detection step 312 in which the air in the chamber flows along the second flow path 32. The adsorption step 311 and the first detection step 312 may be independent from each other, and may be performed in sequence, in parallel, or in parallel with certain time difference. In the adsorption step 311, the absorbent 24*a* may concentrate a target gas included in the circulating air. Furthermore, in the first detection step 312, the sensor device 27 may detect gases included in the circulating air.

Figure 5:
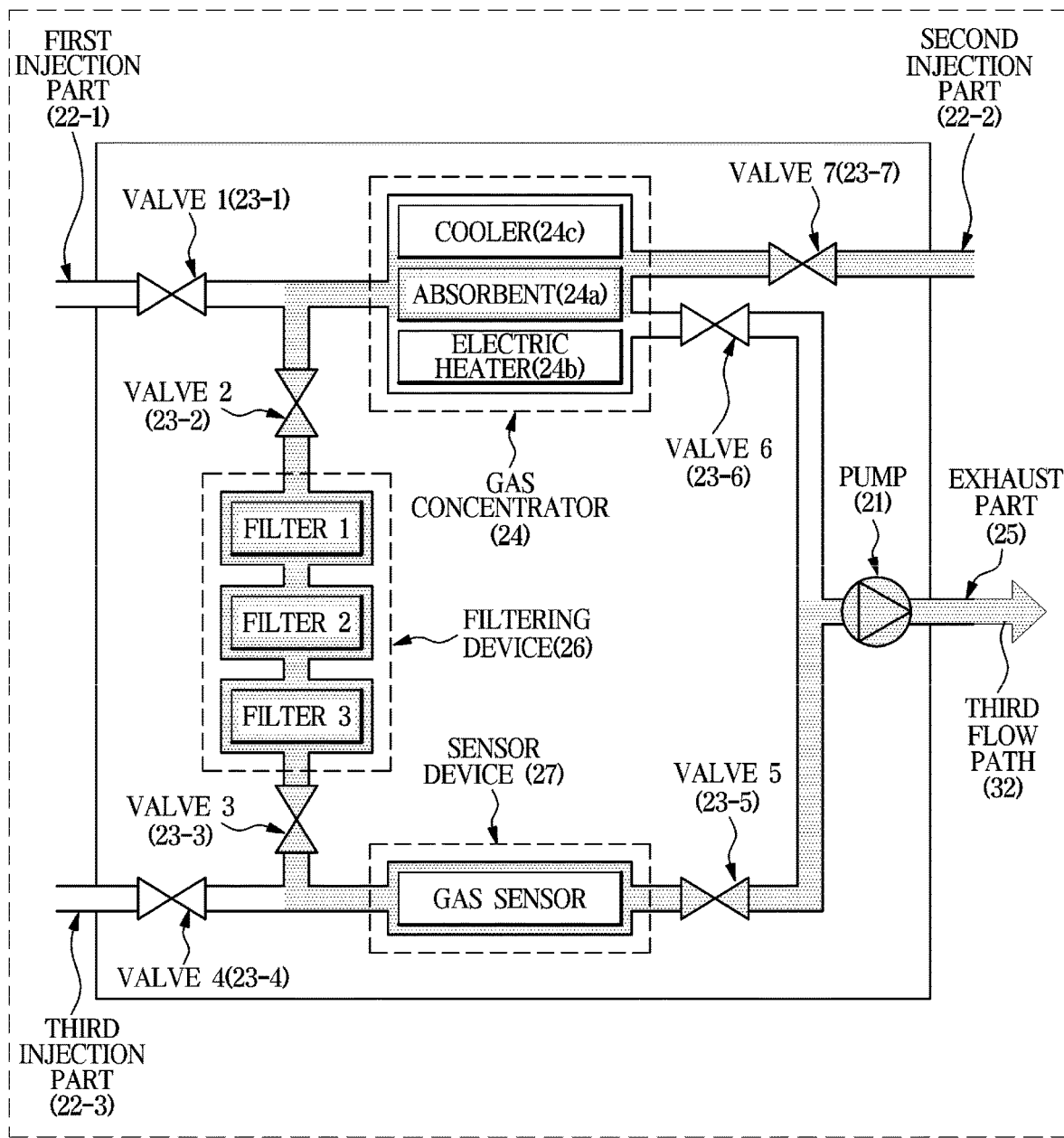
FIG. 5 shows a circulation process of air inside a gas detection device, according to an embodiment of the disclosure.

When the circulation step 310 is performed, the article storage apparatus 10 may perform a heat desorption step 320, a path control step 330, a filtering step 340, a second detection step 350, and a cooling step 360 as the air in the chamber is flowing along the third flow path 33, as shown in FIG. 5.

In the heat desorption step 320, the electric heater 24*b* may apply heat to the absorbent 24*a* to desorb gases adsorbed on the absorbent 24*a*.

In the path control step 330, the article storage apparatus 10 may control the path of air such that the desorbed gases pass through the filtering device 26 and the sensor device 27 without being discharged out of the gas detection device 20. For example, the article storage apparatus 10 may use an air path control algorithm to control the air path.

In the filtering step 340, the filtering device 26 may filter out other gases than the target gas to select the target gas from among the desorbed gases.

In the second detection step 350, the sensor device 27 may detect the target gas and measure a concentration level of the target gas. In this case, the second detection step 350 may have a relatively long detection cycle as compared to the first detection step 312. For example, when the first detection step 312 is a real-time detection step having a sampling period of a second or less, the detection cycle of the second detection step 350 may be between one hour and one day. In this case, the first detection step 312 may be performed to mainly detect high concentration gases, and the second detection step 350 may be performed to detect low concentration gases (e.g., in tens of ppb).

In the cooling step 360, the cooler 24c may cool the heated absorbent 24a.

The article storage apparatus 10 may identify at least one of a type or a condition of the article in the chamber based on a concentration level of the gas measured in the first detection step 312 or the second detection step 350.

Figure 4B:
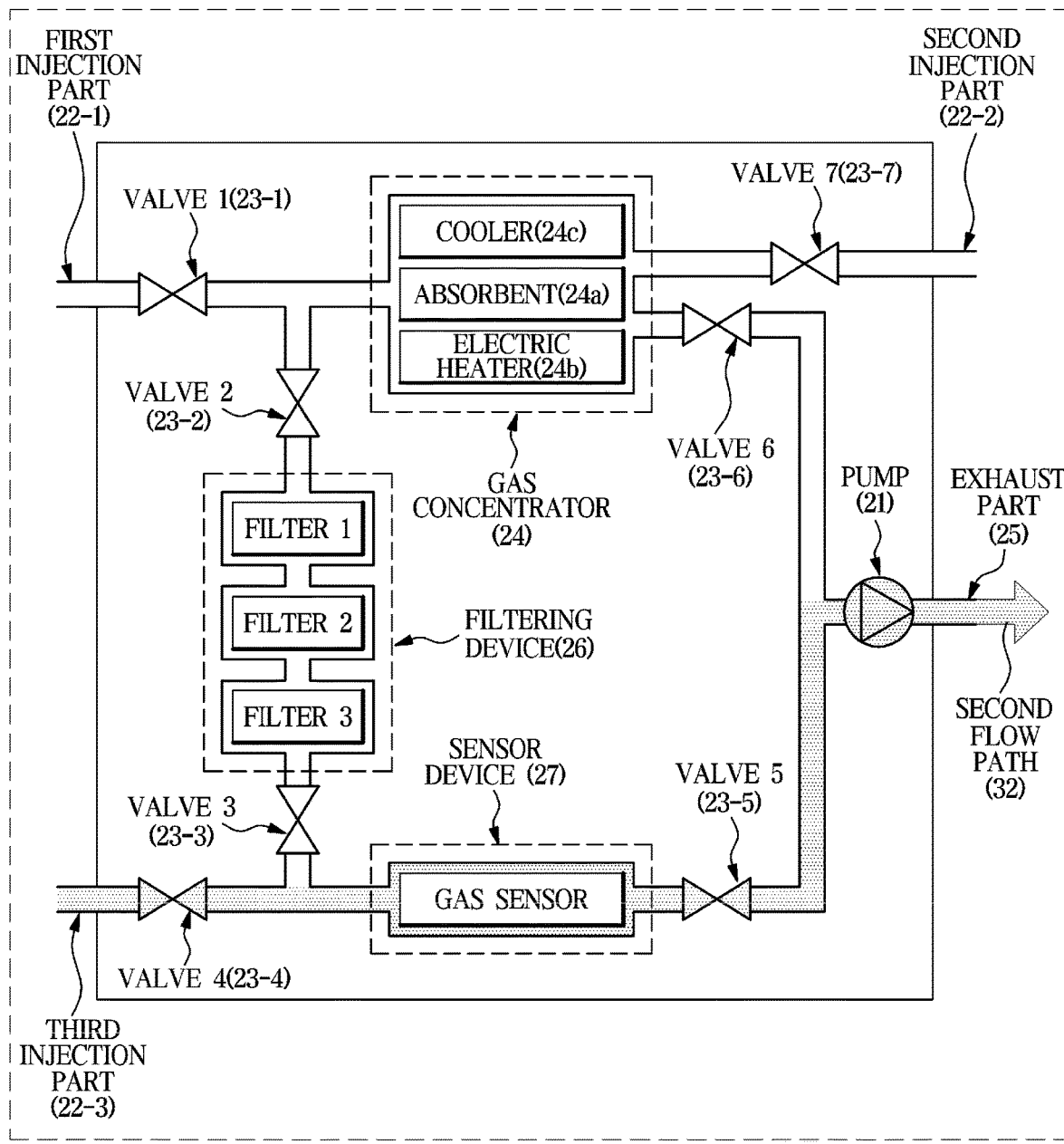
FIG. 4B shows a circulation process of air inside a gas detection device, according to an embodiment of the disclosure.

FIGS. 4A, 4B, and 5 show a circulation process of air inside the gas detection device 20, according to an embodiment of the disclosure.

Referring to FIG. 4A, the air in the chamber may be injected through the first injection part 22-1. The air injected through the first injection part 22-1 may flow along the first flow path 31. For this, the first valve 23-1 and the sixth valve 23-6 may be opened under the control of the processor 11 or the processor of the gas detection device 20. The air circulating along the first flow path 31 may reach the gas concentrator 24. In the gas concentrator 24, a target gas (e.g., a gas related to food freshness) included in the injected air may be concentrated on the absorbent 24a. The air that has passed the gas concentrator 24 with at least a portion of the target gas removed may be discharged to the outside through the exhaust part 25 along the first flow path 31.

In the meantime, as shown in FIG. 4B, the air in the chamber may be injected through the third injection part 22-3. The air injected through the third injection part 22-3 may flow along the second flow path 32. For this, the fourth valve 23-4 and the fifth valve 23-5 may be opened under the control of the processor 11 or the processor of the gas detection device 20. The air flowing along the second flow path 32 may reach the sensor device 27. The sensor device 27 may perform the first detection step 312 (see FIG. 3) for detecting gases having a certain concentration level or higher. The air that has passed the sensor device 27 may be discharged to the outside through the exhaust part 25 along the second flow path 32. In this case, the processor 11 may identify at least one of a type or a condition of an article in the chamber based on a concentration level of the gas measured by the sensor device 27.

The target gas may be concentrated on the absorbent 24a, and as temperature of the electric heater 24b rises in certain time (e.g., of a few minutes), the target gas adsorbed on the absorbent 24a may be desorbed by the heat energy. For this, when a certain time has passed after the target gas is concentrated on the absorbent 24a, the first valve 23-1, the second valve 23-2, the sixth valve 23-6, and the seventh valve 23-7 may be closed to block the heat of the gas concentrator 24 under the control of the processor 11 or the processor of the gas detection device 20.

Subsequently, under the control of the processor 11 or the processor of the gas detection device 20, the first valve 23-1, the fourth valve 23-4, and the sixth valve 23-6 may be closed while the seventh valve 23-7, the second valve 23-2, the third valve 23-3, and the fifth valve 23-5 may be opened.

Accordingly, as shown in FIG. 5, the air in the chamber injected through the second injection part 22-2 may flow along the third flow path 33.

As the air in the chamber is injected through the second injection part 22-2, the target gas desorbed from the absorbent 24a may flow to the filtering device 26. The filtering device 26 may separate and filter out other gases than the target gas. The target gas filtered from the filtering device 26 may be injected to the sensor device 27. The sensor device 27 may perform the second detection step 350 (see FIG. 3) for sensing the injected target gas and measuring a concentration level of the target gas. The air that has passed the sensor device 27 may be discharged to the outside through the exhaust part 25 along the second flow path 33. In this case, the processor 11 may identify at least one of a type or a condition of an article in the chamber based on a concentration level of the gas measured by the sensor device 27.

When a certain time (e.g., of a few minutes) passes after the temperature of the electric heater 24b of the gas concentrator 24 rises, the electric heater 24b of the gas concentrator 24 may be deactivated and the cooler 24c may be activated. Accordingly, desorption of the target gas from the absorbent 24a may be stopped.

Again, when the second valve 23-2, the third valve 23-3, the fourth valve 23-4, the fifth valve 23-5, and the seventh valve 23-7 are closed while the first valve 23-1 and the sixth valve 23-6 are opened under the control of the processor 11 or the processor of the gas detection device 20, circulation of the air in the chamber flowing along the first flow path 31 and undergoing the adsorption step 311 of FIG. 3 of the gas concentrator 24 may be repeated, as shown in FIG. 4A. In this case, when the fourth valve 23-4 and the fifth valve 23-5 are further opened, circulation of the air in the chamber flowing along the second flow path 32 and undergoing the first detection step 312 of FIG. 3 may be repeated, as shown in FIG. 4B.

Figure 6:
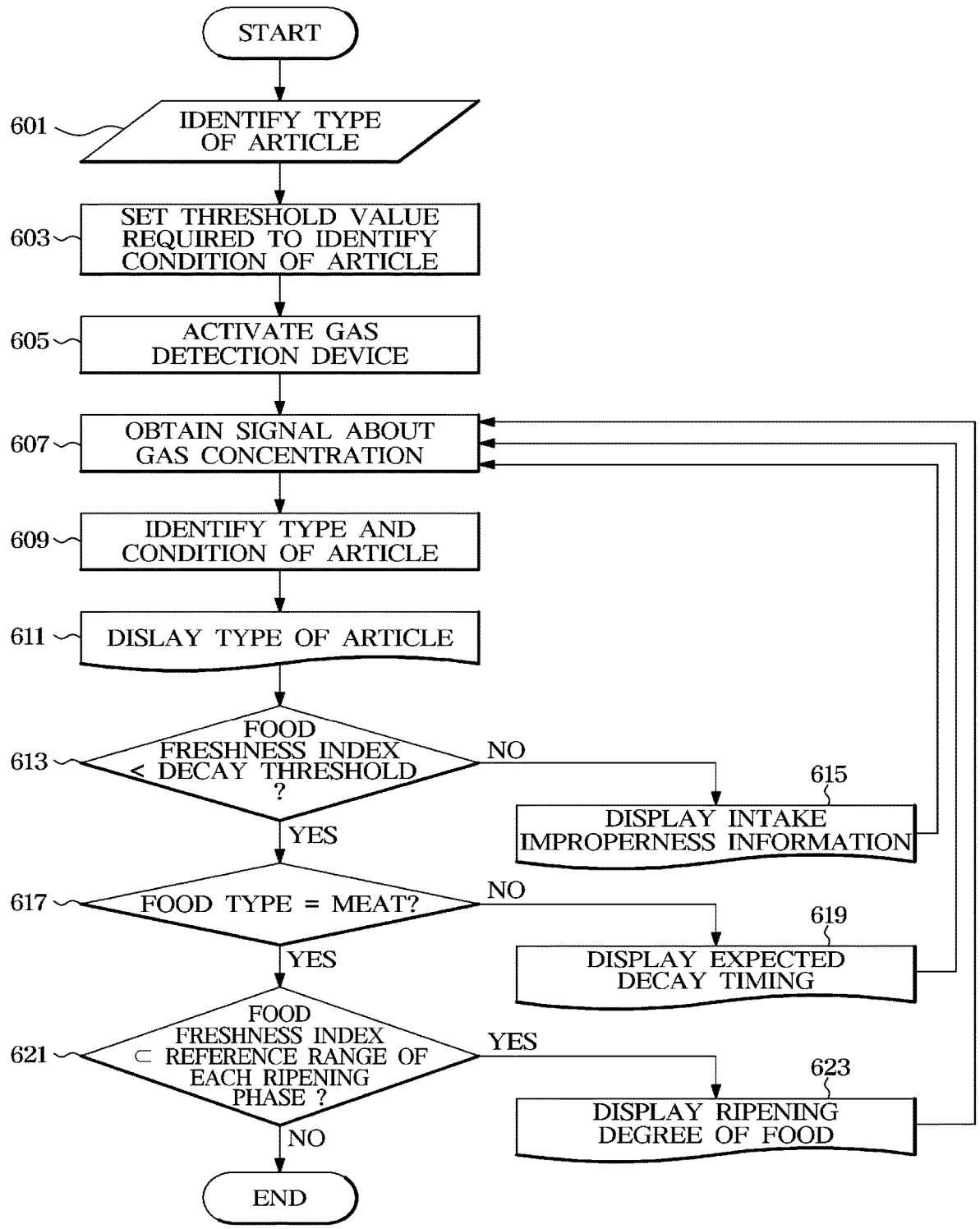
FIG. 6 is a flowchart for determining a condition of an article, according to an embodiment of the disclosure.

FIG. 6 is a flowchart for determining a condition of an article, according to an embodiment of the disclosure.

In 601 of FIG. 6, the article storage apparatus 10 may identify the type of an article in the chamber. The article may be, for example, food, a garment, micro organism, or an animal, without being limited thereto.

The article storage apparatus 10 may identify a type of the article based on a user input entering or selecting the type of the article through the user input device 12.

For example, the user may make a touch input about a type of the article on a touch panel (not shown) provided by the article storage apparatus 10, or make an input by utterance about the type of the article through a microphone (not shown).

When the type of the article is identified, in 603 of FIG. 6, the article storage apparatus 10 may set threshold values required to identify a condition of the article. For example, the article storage apparatus 10 may set at least one of air circulation time in the gas detection device 20, operation time of each step of FIG. 3 (e.g., the circulation step 310, the adsorption step 311, the first detection step 312, the heat desorption step 320, the path control step 330, the filtering step 340, the second detection step 350, the cooling step 360, etc.), a weight for the target gas, a decay threshold, a range for each ripening phase, or a method of identifying a condition of the article, depending on the type of article.

In an embodiment of the disclosure, the article storage apparatus 10 may set the decay threshold. For example, when the type of the article is meat and a volatile basic nitrogen (VBN) content of the air in the chamber is 20 mg % or more, the article storage apparatus 10 may set the decay threshold such that the condition of the article is identified as spoiled. In another example, when the type of the article is beef sirloin kept for a certain period at the temperature of 3 to 4 degrees and a VBN content of the air in the chamber is 9 mg % or more, the article storage apparatus 10 may set the decay threshold such that the condition of the beef sirloin is identified as spoiled. In yet another example, when there is 250 grams (g) of beef sirloin in a volume, e.g., 0.0237 m$^3$ of pantry used for meat storage, and about 800 ppb or more ammonia is measured in the air in the chamber, the article storage apparatus 10 may set the decay threshold such that the condition of the beef sirloin in the pantry is identified as spoiled.

In an embodiment of the disclosure, the article storage apparatus 10 may set the range for each ripening phase. For example, when the type of the article is meat, the article storage apparatus 10 may divide gas concentration from right after butchery to right before the aforementioned decay threshold into three to four levels to set a range for each ripening phase.

In 605 of FIG. 6, the article storage apparatus 10 may activate the gas detection device 20. For example, the article storage apparatus 10 may turn on the gas detection device 20 or switch the gas detection device 20 from ready mode (or sleep mode) into wake-up mode.

In 607 of FIG. 6, the article storage apparatus 10 may obtain a signal about the gas concentration measured by the sensor device 27 of the gas detection device 20.

In 609 of FIG. 6, the article storage apparatus 10 may identify the type of an article based on the obtained signal. For example, the article storage apparatus 10 may identify a type of food based on a signal pattern of the gas measured using two or more kinds of multiple sensor arrays included in the sensor device 27.

For signal pattern analysis of a gas, there may be a principle component analysis method. The article storage apparatus 10 may store information in advance about a multi-dimensional graph as shown in FIG. 7 that has axes of two or more kinds of principle components, based on the values obtained from experimental materials measured by two or more kinds of sensors (e.g., material-specific values, characteristic vectors, etc.).

Figure 7:
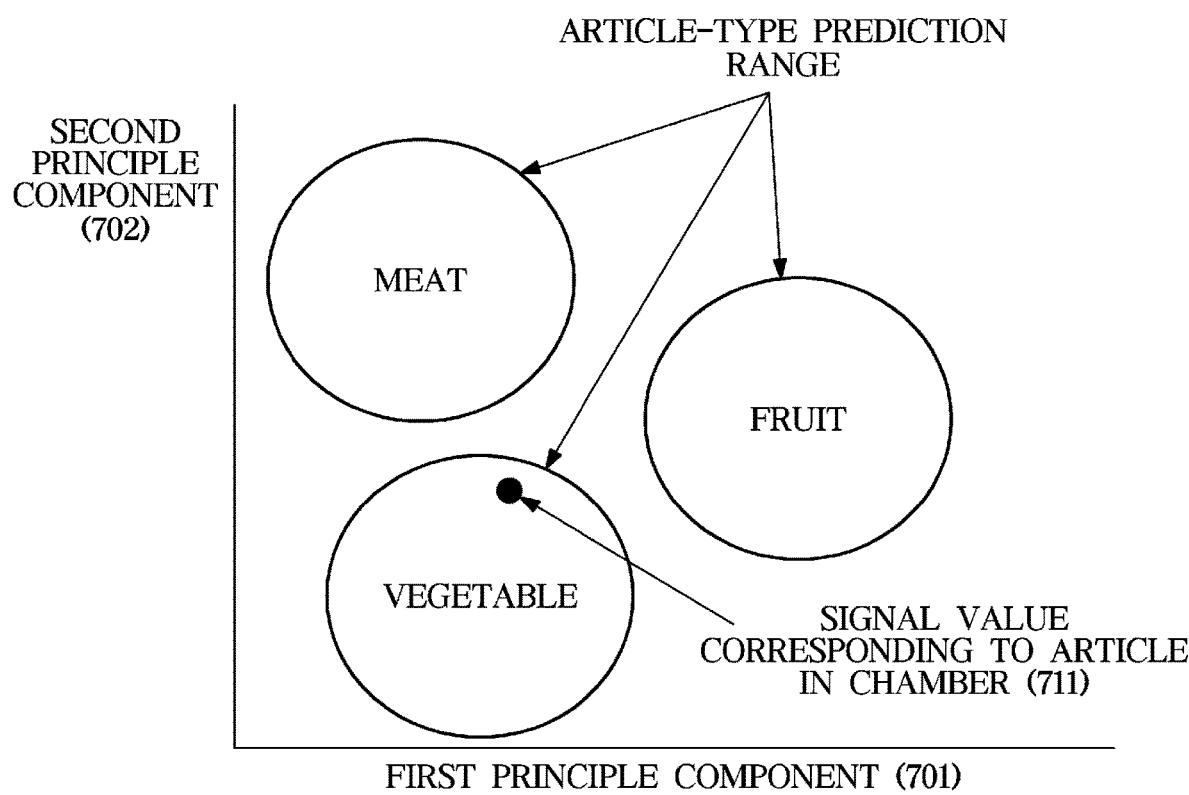
FIG. 7 is a multi-dimensional graph enabling prediction of a type of an article, according to an embodiment of the disclosure.

Referring to FIG. 7, the multi-dimensional graph may include article-type prediction ranges within which to predict a type of an article from a first principle component value and a second principle component value. The article-type prediction range may gather values having similar attributes into a group using various types of clustering methods. The clustering method may include, but not exclusively to, e.g., K-means clustering, Mean-Shift clustering, DBSCAN clustering, GMM clustering, or SVM clustering, or may use a modern deep-learning neural network artificial intelligence algorithm.

In this case, the article storage apparatus 10 may predict a type of the article based on a signal value measured by the sensor device 27. According to the multi-dimensional graph of FIG. 7 for schematic explanation, the article storage apparatus 10 may project a signal value (e.g., (the first principle component value, the second principle component value)) corresponding to an article in the chamber measured by the sensor device 27 onto a point 711 in the multi-dimensional graph. In this case, when the point 711 belongs to a distribution range of vegetables, the article storage apparatus 10 may identify the type of the article stored in the chamber as a vegetable.

The article-type prediction range is just an example for convenience of explanation, and various types of article-type prediction ranges taking into account gas components that may be emitted from each article may be set based on the multi-dimensional graph having axes of two or more kinds of principle components. Although meat, fruit, and vegetables are subjects for the article type ranges on the multi-dimensional graph of FIG. 7, the disclosure is not limited thereto and more various types of article (e.g., beef, pork, fish, vegetable or fruit) may be the subjects for setting the article-type prediction ranges.

When the type of the article is identified, the article storage apparatus 10 may display the type of the article in 611 of FIG. 6. In this case, the type of article to be displayed may be identical to a type of article input by the user in 601 of FIG. 6, or may include a more detailed type of article. Alternatively, the type of article may include a new type of article that is not input by the user.

For example, a type of article predicted based on a signal value measured by the sensor device 27 may be additional information that is supplementary to a type of the article, and may have nothing to do with the threshold value required for activation of the gas detection device 20 as described above in 603 of FIG. 6.

In 609 of FIG. 6, the article storage apparatus 10 may identify a condition of the article based on the obtained signal.

The condition of the article may include, for example, freshness of the article, a contamination level of the article, whether the article is spoiled or a ripening level, without being limited thereto.

For example, the article storage apparatus 10 may identify the freshness of the article (e.g., freshness of a food) based on the following equation 1. In the equation 1, assume that there are a plurality of target gases: Gas A, Gas B, and Gas C.

$$\text{Freshness index of food} = (\text{a concentration level of Gas } A \times \text{a weight for Gas } A) + (\text{a concentration level of Gas } B \times \text{a weight for Gas } B) + (\text{a concentration level of Gas } C \times \text{a weight for Gas } C), \quad \text{[Equation 1]}$$

where the freshness of the article (e.g., freshness of the food) is identified, the article storage apparatus 10 may determine whether the freshness index of the food is less than a decay threshold, in 613 of FIG. 6.

When it is determined that the freshness index of the food is equal to or greater than the decay threshold, the article storage apparatus 10 may display intake improperness information indicating that it is impossible to eat the food, in 615 of FIG. 6.

In 617 of FIG. 6, the article storage apparatus 10 may determine whether the type of the food is one that is able to ripen (e.g., meat).

When the food is not able to ripen, the article storage apparatus 10 may display expected decay timing information of the food, in 619 of FIG. 6. For example, the article storage apparatus 10 may predict the expected decay timing of the food by predicting a rate of change over time of the freshness index of the food.

When the type of food is one that is able to ripen, the article storage apparatus 10 may determine which one of the preset ranges of ripening phases for the food the freshness index of the food belongs to, in 603 of FIG. 6.

When the ripening phase of food is determined, the article storage apparatus 10 may display the ripening information of the food, in 623 of FIG. 6. For example, the ripening phase of the food may be divided into at least three or more phases, in which case, the ripening phase of the food in the chamber may be displayed by number, color, or symbol.

Figure 8:
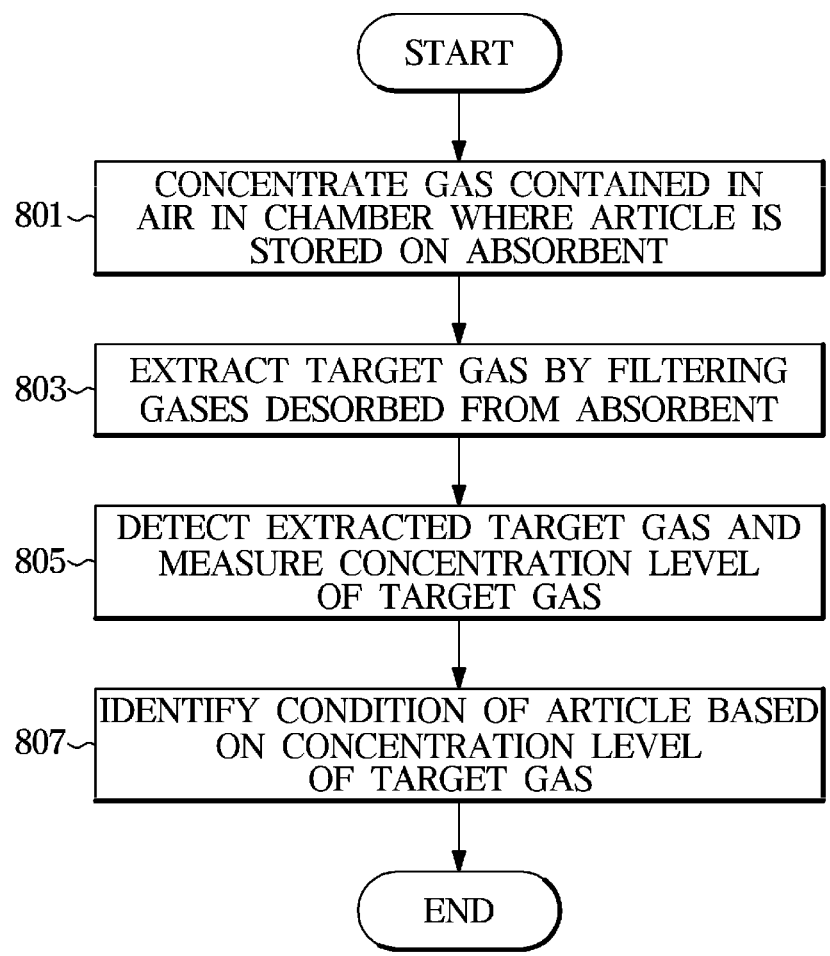
FIG. 8 is a flowchart illustrating how an article storage apparatus identifies a condition of an article, according to an embodiment of the disclosure.

FIG. 8 is a flowchart illustrating how an article storage apparatus identifies a condition of an article, according to an embodiment of the disclosure.

In 801, the article storage apparatus 10 may concentrate gases contained in the air in the chamber where the article is stored on the absorbent 24a.

In 803, the article storage apparatus 10 may extract a target gas by filtering the gases desorbed from the absorbent 24a.

In 805, the article storage apparatus 10 may detect the extracted target gas and measure a concentration level of the target gas.

In 807, the article storage apparatus 10 may identify a condition of the article based on the measured concentration level of the target gas.

In an embodiment of the disclosure, the article storage apparatus 10 may close or open at least one of the plurality of valves that guides the air in the chamber along a flow path such that the air passes the gas concentrator 24 including the absorbent 24a along the first flow path 31. Furthermore, the article storage apparatus 10 may close or open at least one of the plurality of valves such that the gases desorbed from the absorbent 24a pass the filtering device 26 for gas filtering and the sensor device 27 for detecting a target gas along the third flow path 33, which is different from the first flow path 31.

In an embodiment of the disclosure, the article storage apparatus 10 may detect all the gases contained in the air in the chamber while the gases contained in the air are being concentrated, and identify at least one of a type and a condition of the article based on the concentration level of all the detected gases.

In an embodiment of the disclosure, the article storage apparatus 10 may close or open at least one of the plurality of valves such that the air in the chamber passes the sensor device 27 for detecting all the gases along the second flow path 32.

In an embodiment of the disclosure, the article storage apparatus 10 may desorb the gases adsorbed on the absorbent 24a by heating the absorbent 24a and then cool the heated absorbent 24a.

In an embodiment of the disclosure, the article storage apparatus 10 may identify a type of the article in the chamber based on a user input, and set threshold values required for identifying a condition of the article.

In an embodiment of the disclosure, the article storage apparatus 10 may display article condition information indicating a condition of the article.

Figure 9:
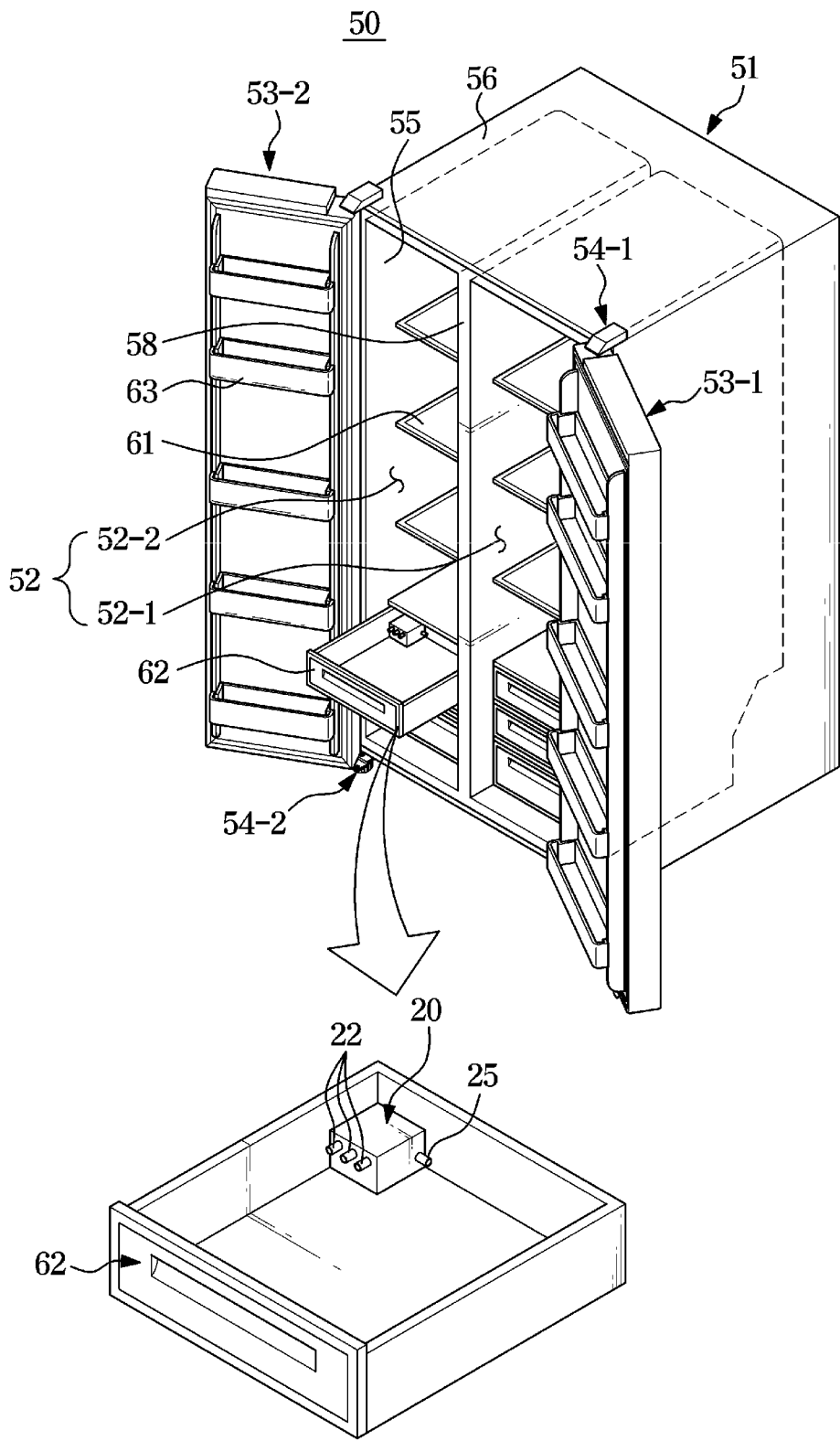
FIG. 9 is a perspective view of an article storage apparatus, according to an embodiment of the disclosure.
Figure 10:
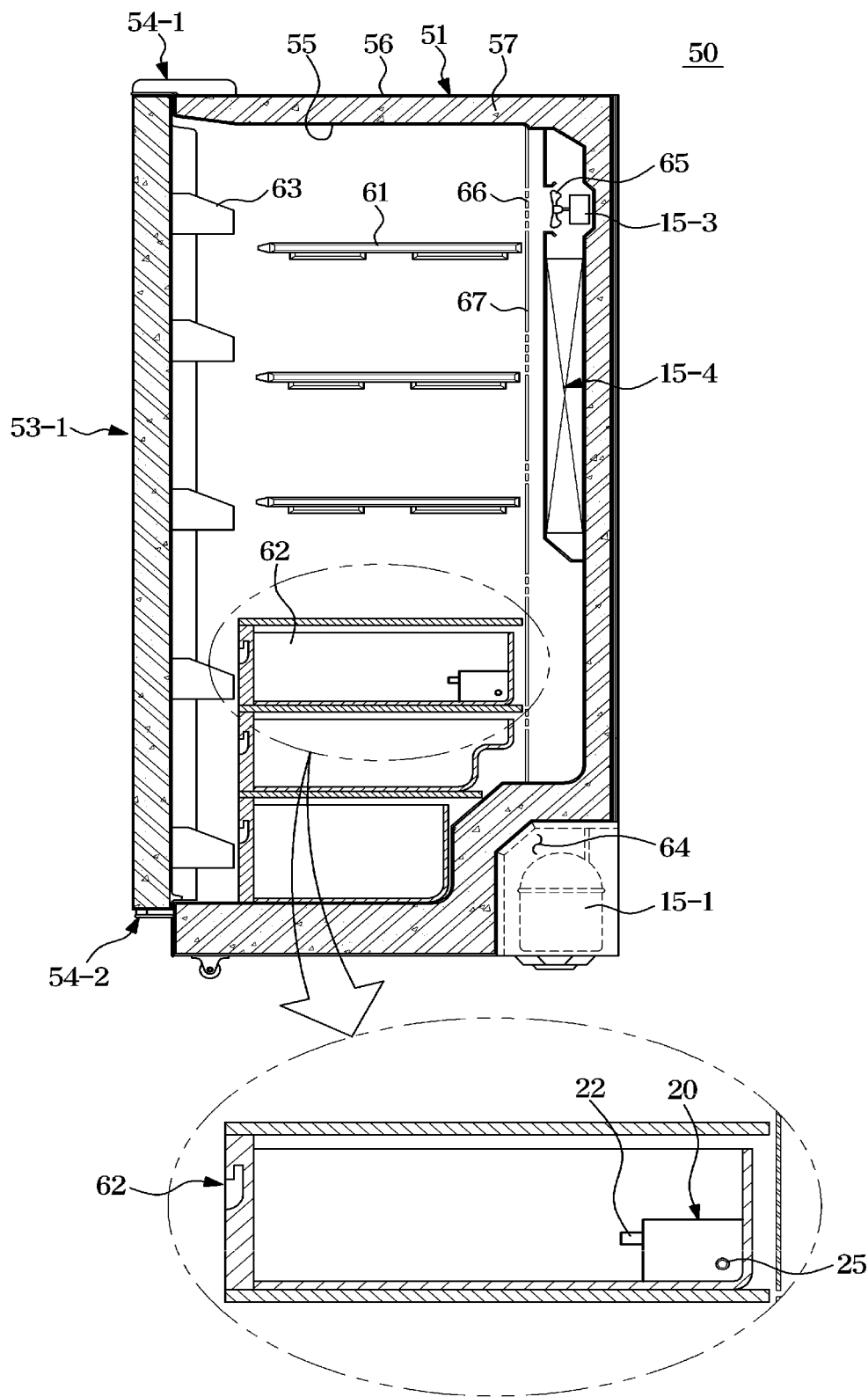
FIG. 10 is a side cross-sectional view of an article storage apparatus, according to an embodiment of the disclosure.

FIG. 9 is a perspective view of the article storage apparatus 10 equipped with the gas detection device 20, according to an embodiment of the disclosure, and FIG. 10 is a side cross-sectional view of the article storage apparatus 10 equipped with the gas detection device 20, according to an embodiment of the disclosure.

In FIGS. 9 and 10, the article storage apparatus 10 may be a refrigerator 50. Referring to FIGS. 9 and 10, the refrigerator 50 includes a main body 51 that defines an exterior, a storeroom 52 arranged in the main body 51 with open front, doors 53-1 and 53-2 pivotally mounted on the main body 51 to open or close the open front of the storeroom 52, and an upper hinge 54-1 and a lower hinge 54-2 for the doors 53-1 and 53-2 to be pivotally mounted on the main body 51.

The main body 51 may include an inner case 55 that forms the storeroom 52 and an outer case 56 that forms the exterior, and an insulation 57 may be foamed between the inner case 55 and the outer case 56 for preventing cold air from leaking out of the storeroom 52.

The main body 51 may also include a partition wall 58 that divides the storeroom 52 into a fridge 52-1 and a freezer 52-2 in the left-and-right direction. For example, the fridge 52-1 may be arranged on the right of the main body 51 and the freezer 52-2 may be arranged on the left of the main body 51.

In the storeroom 52, there may be a plurality of shelves 61 and containers 62 to store foods.

The storeroom 52 may be opened or closed by the doors 53-1 and 53-2 pivotally mounted on the main body 51, and specifically, the fridge 52-1 and the freezer 52-2 are opened or closed by a fridge door 53-1 and a freezer door 53-2, respectively.

The fridge door 53-1 and the freezer door 53-2 may be pivotally coupled to the main body 51 by the upper hinge 54-1 on the top of the main body 51 and the lower hinge 54-2 on the bottom of the main body 51.

On the rear sides of the fridge and freezer doors 53-1 and 53-2, a plurality of door guards 63 are arranged to contain food.

A machine room 64 where a compressor 15-1 for compressing refrigerant and a condenser 52-2 (see FIG. 11) for condensing the compressed refrigerant are installed may be provided on the lower side of a rear portion of the main body 51.

The compressor 15-1 and the condenser 15-2 provided in the machine room 64 may define a cooler 15 together with an expander 15-3 and an evaporator 15-4. Cold air produced in the cooler 15 is supplied into the storeroom 52. For example, a blower fan 65 and a cold air duct 67 having discharge holes 66 formed therethrough may have the cold air produced in the evaporator 15-4 discharged into the storeroom 52.

In FIGS. 9 and 10, the gas detection device 20 may be provided in the storeroom 52 to detect the gas contained in the air in the storeroom 52. Alternatively, the gas detection device 20 may be arranged in the container 62, or on the plurality of shelves 61, or in the door guard 63. In another embodiment of the disclosure, there may be one or more gas detection devices 20 provided in the storeroom 52. For example, the plurality of gas detection devices 20 may be arranged in the container 62, or on the plurality of shelves 61, or in the door guards 63. The gas detection device 20 may be fixedly or detachably provided in a space in the storeroom 52. The injection part 22 through which the air in the chamber is injected and the exhaust part 25 through which the injected air is discharged may be arranged on the outside of the gas detection device 20.

FIG. 11 is a block diagram of an article storage apparatus, according to another embodiment of the disclosure.

In FIG. 11, the article storage apparatus 10 may be the refrigerator 50.

Referring to FIG. 11, the refrigerator 50 may include the user input device 12, the cooler 15, a sensor device 14 for measuring the inside or outside air temperature of the main body 51, measuring opening or closing of the doors 30, etc., a memory 13 for storing results of the measurement performed by the sensor device 14 and various types of data, and a processor 11 for controlling the respective components of the refrigerator 50.

The cooler 15 supplies cold air into the storeroom 52. Specifically, the cooler 15 may keep the temperature of the storeroom 52 within a set range by using evaporation of the refrigerant.

The cooler 15 may include the compressor 15-1 for compressing a gaseous refrigerant, the condenser 15-2 for changing the compressed gaseous refrigerant into a liquid state, the expander 15-3 for depressurizing the liquid refrigerant, and the evaporator 15-4 for changing the depressurized liquid refrigerant into a gaseous state. A cycle including a series of operations of the components of the cooler 15 may be referred to as a cooling cycle.

The cooler 15 may cool the air in the storeroom 52 using a phenomenon in which a liquid refrigerant absorbs thermal energy of ambient air while changing from liquid to gaseous state.

The evaporator 15-4 may include a tube in which the refrigerant flows and a plurality of cooling fins 120 coupled to the outer circumferential surface of the tube to facilitate heat exchange between the refrigerant flowing through the tube and outside air. In the cooling cycle, the liquid refrigerant at a low temperature and low pressure is evaporated in the evaporator 15-4 while moving along the tube. The evaporator 15-4 may absorb heat required for evaporation of the refrigerant from the surrounding air.

The user input device 12 may receive various input commands from the user.

The user input device 12 may receive a target temperature for the internal temperature to be maintained at the storeroom 52. Furthermore, the user input device 12 may receive a type of the article in the chamber. The user input device 12 may receive various other input commands than the aforementioned command. The user input unit 12 may include many different buttons or switches, a pedal, a keyboard, a mouse, a track ball, various levers, a handle, a stick, or some hardware devices for the user input. The user input device 12 may also include a Graphical User Interface (GUI), i.e., a software device, such as a touch pad for the user input. The touch pad may be implemented with a Touch Screen Panel (TSP), thus forming an interlayer structure with a display device (not shown).

The display device may also be used for the user input device 120 when implemented with the TSP that forms the interlayer structure with the touch pad.

The sensor device 14 may include an inner temperature sensor 14-1 for detecting inside temperature of the storeroom 52, and an outer temperature sensor 14-2 for detecting various temperatures required for the cooling cycle and the defrost cycle of the refrigerator 50, and the gas detection device 20 including a gas sensor for detecting gases contained in the air in the storeroom 52.

The inner temperature sensor 14-1 may detect respective temperatures of spaces defined by dividing the storeroom 52 by the partition wall 58 and the shelves 61, and provide an electric signal corresponding to the detected temperature to the processor 11. Each of the inner temperature sensors 14-1 may include a thermistor temperature sensor that uses semiconductor resistance changed by the temperature.

The outer temperature sensor 14-2 may detect temperature around where the refrigerator 50 is installed, i.e., an ambient temperature. The outer temperature sensor 14-2 may also detect the temperature required for operation of the cooling cycle, e.g., the temperature for identifying operation of each component of the cooler 15. The outer temperature sensor 14-2 may provide the detected temperature to the processor 11.

The outer temperature sensor 14-2 may be implemented with a contact-type temperature sensor or a non-contact-type temperature sensor depending on the detection method. Specifically, the outer temperature sensor 14-2 may be implemented not only with the thermistor temperature sensor as described above in connection with the inner temperature sensor 14-1 but also at least one of a resistance temperature detector (RTD) temperature sensor that uses metal resistance changed by temperature, a thermocouple temperature sensor that uses electromotive force produced across the junction between two types of metal wires having different substances, and an integrated circuit (IC) temperature sensor that uses current-voltage characteristics of a P-N junction or a voltage across a transistor changed by temperature. The outer temperature sensor 14-2 may, however, include other various temperature sensors.

The sensor device 14 may further include other various sensors, such as a sensor for detecting whether the doors 53-1 and 53-2 are opened or closed, an image sensor for capturing an image of the inside of the storeroom 52 and converting the image into an electric signal, etc., as well in addition to the temperature sensor and the gas sensor included in the gas detection device 20.

The memory 13 may store a program and/or data, and collect a program and/or data through a contact terminal capable of accessing an external storage medium.

The program may include a plurality of instructions combined to perform a particular function, and the data may be processed according to the plurality of instructions included in the program. Furthermore, the program and/or data may include a system program and/or system data directly related to operation of the refrigerator 50, and an application program and/or application data for providing convenience and entertainment for the user.

The memory 13 may be implemented with at least one of a non-volatile memory device, such as cache, read only memory (ROM), programmable ROM (PROM), erasable programmable ROM (EPROM), electrically erasable programmable ROM (EEPROM), a volatile memory device, such as random access memory (RAM), or a storage medium, such as hard disk drive (HDD) or compact disk (CD) ROM, without being limited thereto.

The memory 13 may store and output the program and/or data to the processor 11. The memory 13 may store a program and/or data that may be executed by the processor 11 to perform an operation as will be described below.

The processor 11 may perform general operation of the refrigerator 50 (e.g., a cooling cycle operation, a defrost cycle operation, etc.). The processor 11 may perform general operation of the refrigerator 50 (e.g., a cooling cycle operation, a defrost cycle operation, etc.). For example, the processor 11 may create a control signal for the components of the cooler 15 that operate in the cooling cycle based on the program and/or data stored in the memory 13.

The processor 50 may include a memory for temporarily storing data of the refrigerator 50, a core for performing logic operation and arithmetic operation, and a register for storing the data resulting from the operation.

At least one component may be added to or deleted from what is shown in FIG. 11 to correspond to the performance of the refrigerator 50. Furthermore, mutual positions of the components may be changed to correspond to the performance or structure of the system.

In an embodiment of the disclosure, the refrigerator 50 may further include a communication device (not shown) for performing communication with an external device or the gas detection device 20. For example, the communication device may receive various control commands from a server (not shown) managed by the manufacturer and apply them to operate the refrigerator 50. Alternatively, the communication device may receive a sensor value from the gas detection device 20 and send the sensor value to the processor 11. The processor 11 may identify freshness of a food (e.g., whether it is spoiled or ripens) based on the received sensor value. Besides, the communication device may further perform various operations such as transmitting an image of the inside of the storeroom captured by a camera (not shown) to e.g., user equipment.

The communication device may include one or more components that enable communication with an external device, for example, at least one of a short-range communication module, a wired communication module, and a wireless communication module.

The short-range communication module may include various short range communication modules for transmitting and receiving signals within a short range over a wireless communication network, such as Bluetooth module, an infrared communication module, a radio frequency identification (RFID) communication module, a wireless local access network (WLAN) communication module, a near field communication (NFC) module, a Zigbee communication module, etc.

The wired communication module may include not only one of various wired communication modules, such as a local area network (LAN) module, a wide area network (WAN) module, or a value added network (VAN) module, but also one of various cable communication modules, such as a universal serial bus (USB), a high definition multimedia interface (HDMI), a digital visual interface (DVI), recommended standard (RS) 232, a power cable, or a plain old telephone service (POTS).

The wireless communication module may include a wireless fidelity (WiFi) module, a wireless broadband (Wibro) module, and/or any wireless communication device for supporting various wireless communication schemes, such as a global system for mobile communication (GSM) module, a code division multiple access (CDMA) module, a wideband code division multiple access (WCDMA) module, a universal mobile telecommunications system (UMTS), a time division multiple access (TDMA) module, a long term evolution (LTE) module, etc.

In the specification, the term "module", "device", "member", or "block" may refer to a unit implemented in hardware, software, or firmware, and may be interchangeably used with e.g., logic, logic block, part, or circuit. The module may be an integral part that performs one or more functions, or a minimum unit or a portion of the part. Furthermore, the module may be implemented in hardware such as a field programming gate array (FPGA) and an application-specific integrated circuit (ASIC).

Various embodiments of the disclosure may be implemented in software including one or more instructions stored in a storage medium that is readable by a machine (e.g., the article storage apparatus 10 or the gas detection device 20). For example, a processor of a device (e.g., the article storage apparatus 10 or the gas detection device 20) may call and execute at least one of the one or more instructions stored in the storage medium. This enables the device to be operated to perform at least one function according to at least one instruction called. The one or more instructions may include codes created by a compiler or codes that may be executed by an interpreter. The machine-readable storage medium may be provided in the form of a non-transitory storage medium. The term 'non-transitory' storage medium may mean that the storage medium is a tangible device which does not include a signal, e.g., electromagnetic waves, without distinguishing between storing data in the storage medium semi-permanently and temporarily.

In an embodiment of the disclosure, the aforementioned method according to the various embodiments of the disclosure may be provided in a computer program product. The computer program product may be a commercial product that may be traded between a seller and a buyer. The computer program product may be distributed in the form of a storage medium (e.g., a compact disc read only memory (CD-ROM)), through an application store (e.g., play store™), directly between two user devices (e.g., smart phones), or online (e.g., downloaded or uploaded). In the case of online distribution, at least part of the computer program product may be at least temporarily stored or arbitrarily created in a storage medium that may be readable to a device such as a server of the manufacturer, a server of the application store, or a relay server.

In various embodiments of the disclosure, each of the aforementioned components (e.g., a module or a program) may include a single entity or multiple entities. In various embodiments of the disclosure, one or more of the aforementioned components or processes may be omitted, or one or more of other components or processes may be added. Alternatively or additionally, a plurality of components (e.g., modules or programs) may be integrated in a single component. In this case, the integrated component may perform one or more functions of the respective components therein equally or similarly to what are performed by the plurality of components before integration. According to various embodiments of the disclosure, processes performed by modules, programs, or other components may be performed sequentially, in parallel, repeatedly, or heuristically, or one or more of the processes may be performed in different order or omitted, or one or more additional processes may be further performed.

According to the disclosure, a gas in a chamber may be concentrated and detected, so that even a low concentration gas (e.g., in tens of ppb) may be detected, thereby enabling a condition of an article to be accurately determined.

Furthermore, a target gas may be extracted and a condition of an article may be identified based on concentration of the target gas, enabling degrees of decay or ripening of the article to be subdivided and identified by concentration of the target gas.

Hence, article condition information indicating a condition of an article (e.g., freshness of a food) may be provided for the user to be able to consider the condition of the food and predict whether it is possible to eat the food and decay timing of the food. Accordingly, the user's health may be safely secured by using the article storage apparatus according to the disclosure.

Several embodiments of the disclosure have been described above, but a person of ordinary skill in the art will understand and appreciate that various modifications can be made without departing the scope of the disclosure. Thus, it will be apparent to those ordinary skilled in the art that the true scope of technical protection is only defined by the following claims.

What is claimed is:

1. An article storage apparatus comprising:
   a chamber;
   a gas concentrator configured to concentrate a target gas contained in air in the chamber where an article is stored;
   a gas filter configured to filter other gases than the target gas among gases desorbed from the gas concentrator;
   a gas sensor configured to sense gases included in air in the chamber;
   a plurality of valves configured to guide a flow path of the air, and
   at least one processor configured to:
      control the gas concentrator to concentrate the gases contained in the air;

close or open at least one of the plurality of valves such that the air passes the gas concentrator along a first flow path, close or open at least one of the plurality of valves such that the air passes the gas sensor along a second flow path, close or open at least one of the plurality of valves such that the gases desorbed from the gas concentrator pass the gas filter and the gas sensor along a third flow path which is different from the first flow path, and identify a condition of the article based on a concentration level of the target gas related to the article measured by the gas sensor when the target gas is extracted as the gases desorbed from the gas concentrator pass the gas filter.

2. The article storage apparatus of claim 1,
wherein the at least one processor is configured to;
while the gases contained in the air is being concentrated in the gas concentrator, identify at least one of a type of the article or a condition of the article based on a concentration level of all gases contained in the air measured by the gas sensor.

3. The article storage apparatus of claim 1, wherein the at least one processor is configured to control at least one of the plurality of valves so that a detection cycle to measure the concentration levels of the gases in the air flowing in the second flow path is shorter than a detection cycle to measure the concentration level of the target gas in the air flowing in the third flow path.

4. The article storage apparatus of claim 1, wherein
the gas concentrator comprises an absorbent, an electric heater, and a cooler, and
the at least one processor is configured to control the electric heater to heat the absorbent to desorb gases adsorbed on the absorbent, and to control the cooler to cool the heated absorbent.

5. The article storage apparatus of claim 1, wherein the target gas comprises at least one of ammonia, trimethylamine or dimethyl sulfide.

6. The article storage apparatus of claim 1, further comprising:
a user input device,
wherein the at least one processor is configured to identify a type of the article based on a user input through the user input device, and set threshold values required to identify the condition of the article based on the type of the article.

7. The article storage apparatus of claim 1, wherein the condition of the article comprises freshness of the article, a contamination level of the article, whether the article is spoiled, or a ripening degree of the article.

8. The article storage apparatus of claim 1, further comprising:
a display device,
wherein the at least one processor is configured to control the display device to display article condition information indicating the condition of the article.

9. A method performed by an article storage apparatus that includes a chamber, a gas sensor, a gas concentrator and a gas filter, the method comprising:

concentrating a target gas included in air in the chamber with an article stored in the chamber on an absorbent of the gas concentrator;

desorbing gases from the gas concentrator;

passing the desorbed gasses through the gas filter to obtain the target gas;

detecting the target gas and measuring a concentration level of the target gas, by the gas sensor; and identifying a condition of the article based on the measured concentration level of the target gas.

10. The method of claim 9, wherein the identifying of the condition of the article comprises closing or opening at least one of a plurality of valves configured to guide a flow path of the air such that the air passes the gas concentrator including the absorbent along a first flow path;

closing or opening at least one of the plurality of valves such that the air passes the gas sensor device configured to detect all the gases along a second flow path; and closing or opening at least one of the plurality of valves such that the gases desorbed from the absorbent pass the gas filter configured to filter the gases and the gas sensor configured to detect the target gas along a third flow path which is different from the first flow path.

11. The method of claim 10, wherein the identifying of the condition of the article comprises:

detecting all gases contained in the air while the gases contained in the air is being concentrated in the gas concentrator; and identifying at least one of a type of the article or a condition of the article based on a concentration level of all the gases detected.

12. The method of claim 10, wherein the method is performed so that a detection cycle to measure the concentration levels of the gases in the air flowing in the second flow path is shorter than a detection cycle to measure the concentration level of the target gas in the air flowing in the third flow path.

13. The method of claim 9, wherein the gas concentrator includes an absorbent, an electric heater, and a cooler, and the method further comprising:

controlling the electric heater to heat the absorbent to desorb gases adsorbed on the absorbent; and controlling the cooler to cool the heated absorbent.

14. The method of claim 9, wherein the target gas comprises at least one of ammonia, trimethylamine or dimethyl sulfide.

15. The method of claim 9, wherein the article storage apparatus includes an input device, and the method further comprises:

identifying a type of the article based on a user input through the input device, and setting threshold values required to identify the condition of the article based on the type of the article.

16. The method of claim 9, wherein the condition of the article comprises freshness of the article, a contamination level of the article, whether the article is spoiled, or a ripening degree of the article.

17. The method of claim 9, wherein the identifying of the condition of the article comprises displaying article condition information indicating a condition of the article.

* * * * *